(12) United States Patent
Perler

(10) Patent No.: US 10,052,209 B2
(45) Date of Patent: Aug. 21, 2018

(54) ANKLE JOINT REPLACEMENT IMPLANT WITH BEARING INTERCHANGEABILITY

(71) Applicant: Adam D. Perler, St. Petersburg, FL (US)

(72) Inventor: Adam D. Perler, St. Petersburg, FL (US)

( * ) Notice: Subject to any disclaimer, the term of this patent is extended or adjusted under 35 U.S.C. 154(b) by 64 days.

(21) Appl. No.: 15/000,952

(22) Filed: Jan. 19, 2016

(65) Prior Publication Data

US 2016/0206437 A1    Jul. 21, 2016

Related U.S. Application Data

(60) Provisional application No. 62/105,023, filed on Jan. 19, 2015.

(51) Int. Cl.
*A61F 2/42* (2006.01)
*A61F 2/30* (2006.01)

(52) U.S. Cl.
CPC .. *A61F 2/4202* (2013.01); *A61F 2002/30369* (2013.01); *A61F 2002/30518* (2013.01); *A61F 2002/30604* (2013.01); *A61F 2002/30879* (2013.01); *A61F 2002/4205* (2013.01); *A61F 2002/4207* (2013.01)

(58) Field of Classification Search
CPC .......... A61F 2/4202; A61F 2002/30369; A61F 2002/4205; A61F 2002/4207
See application file for complete search history.

(56) References Cited

U.S. PATENT DOCUMENTS

2009/0182433 A1 * 7/2009 Reiley .................. A61B 17/15
623/18.11

* cited by examiner

*Primary Examiner* — Brian Dukert
(74) *Attorney, Agent, or Firm* — Bruce J Bowman

(57) ABSTRACT

A polyaxial ankle joint replacement implant has a dual bearing component situated between a tibia attachment component and a talus attachment component. The dual bearing component includes a plate, a superior bearing bonded to the plate and providing translation with the tibia attachment component, and an inferior bearing providing translation with the talus attachment component. The tibia attachment component has peripheral transversely extending flanges that limit movement relative to the superior bearing and vice versa. The plate has a flange on its inferior surface that receives an opening in the inferior bearing, the size of the opening determining an amount of lateral translation. The plate also has unobstructed posterior and/or anterior ends that permit removal and replacement of the inferior bearing post-operative. This allows change from a mobile to fixed bearing (and vice versa), as well as a change in amount of degrees of translation.

17 Claims, 17 Drawing Sheets

ANKLE JOINT REPLACEMENT IMPLANT WITH BEARING INTERCHANGEABILITY

CROSS REFERENCE TO RELATED APPLICATIONS

This non-provisional patent application claims the benefit of and/or priority under 35 U.S.C. § 119 to U.S. Provisional Patent Application Ser. No. 62/105,023 filed Jan. 19, 2015, entitled "Ankle Joint Replacement Implant with Mobile Bearing to Fixed Bearing Interchangeability" the entire contents of which is specifically incorporated herein by this reference.

This non-provisional patent application is also related to and specifically incorporates herein by reference the following publications/documents: 1) U.S. Pat. No. 8,668,743 issued Mar. 11, 2014, titled "Prosthetic Device With Multi-Axis Dual Bearing Assembly and Methods For Resection;" 2) U.S. Provisional Patent Application Ser. No. 61/409,280 filed Nov. 2, 2010, titled "Prosthetic Device with Multi-Axis Dual Bearing Assembly and Methods for Resection" which was the progenitor of U.S. Pat. No. 8,668,743; 3) U.S. patent application Ser. No. 14/453,789 filed Aug. 7, 2014 titled, "Polyaxial Endoprosthetic Ankle Joint Replacement Implant;" and 4) U.S. Provisional Patent Application Ser. No. 61/863,394 filed Aug. 7, 2013, titled "Polyaxial Endoprosthetic Ankle Joint Replacement Implant" which was the progenitor of U.S. patent application Ser. No. 14/453,789.

BACKGROUND OF THE INVENTION

Field of the Invention

The present subject matter is directed generally to joint replacement implants and, more particularly, to multi-axis ankle joint replacement implants.

Background Information

The concept of total ankle arthroplasty has a long and relatively unsuccessful history due to the high failure rate often associated with the original implant devices and implantation techniques. Only recently has total ankle arthroplasty regained some recognition as a viable treatment for limited indications and as a viable alternative to an ankle joint fusion, which is often referred to as the gold standard of treatment. It has been shown that replacement of an ankle joint with an ankle prosthesis can be particularly challenging due to the relatively small articular contact surfaces of the ankle, complex biomechanics of both the ankle and hindfoot joints, limited and risky access to the ankle joint during replacement, and wide variation in patient candidacy. Past flawed design rationale and the above factors have led to a high rate of post-operative complications such as loosening of the ankle prosthesis, subsidence, pain, abnormal ankle prosthesis wear, and/or meniscal/bearing breakdown—often leading to ankle implantation failure.

There are two types of ankle prosthetics for ankle arthroplasty or replacement that are generally available, a fixed bearing ankle prosthetic and a mobile bearing ankle prosthetic. Both types of ankle prosthetics utilize either a three (3) piece and two (2) component design (with the meniscal portion/bearing locking into the tibia plate) or a three (3) piece and three (3) component design (with a mobile/unlocked bearing) including an upper, middle, and lower component (tibia, bearing, and talus component, respectively). Once a particular type is chosen, it is difficult, if not impossible, to revise the surgery and provide another type of implant, particularly if the metal to bone interface(s) is/are not to be disturbed. As well, it is difficult, if not possible, to perform revision surgery on a mobile bearing ankle prosthetic in order to change the amount of translation freedom.

It is therefore apparent from the above that the need exists for an ankle joint replacement implant that allows interchangeability from and/or between a mobile bearing ankle joint replacement implant and a fixed bearing ankle joint replacement implant. It is also apparent from the above that the need exists for an ankle joint replacement implant that allows changeability from a mobile bearing ankle joint implant providing a particular degree of translation to a mobile bearing ankle joint implant providing a different degree of translation.

SUMMARY OF THE INVENTION

The present invention is an ankle joint replacement implant that allows a bearing of the implant to be changed without disturbing the talus bone anchoring component or the tibia bone anchoring component of the implant.

The bearing may be changed post operatively via another operation from a mobile bearing to a fixed bearing and vice versa, or from a mobile bearing of a particular degree of translation to a mobile bearing of another particular degree of translation.

In one form, the bearing is an inferior bearing of a dual bearing component that is situated between the tibia anchoring component and the talus anchoring component. The dual bearing component includes a plate, a superior bearing bonded to the plate and providing translation with the tibia attachment component, and an inferior bearing providing translation with the talus attachment component. The tibia plate has peripheral transversely extending flanges that limit movement relative to the superior bearing and vice versa. The plate has a flange on its inferior surface that receives an opening in the inferior bearing, the size of the opening determining an amount of lateral translation. The plate also has unobstructed posterior and/or anterior ends that permit removal and replacement of the inferior bearing post-operative. This allows change from a mobile to fixed bearing (and vice versa), as well as a change in amount of degrees of translation In one form, the ankle joint replacement implant is modular in construction such that one or more of the dual bearing component for a fixed or mobile bearing type can be replaced with one or more dual bearing component(s) for the mobile or fixed bearing type respectively without disturbing the metal to bone interface between the tibia component, and/or between the talus component.

In one form, the ankle joint replacement implant has a tibia anchoring component, a talus anchoring component, and a dual bearing component positioned between the tibia and talus anchoring components. The dual bearing component includes a superior bearing providing gliding translation between it and the tibia anchoring component, an inferior bearing providing gliding translation between it and the talus anchoring component, and a bearing component plate that provides a base or foundation for the superior and inferior bearings. The superior bearing is bonded to the bearing component plate while the inferior bearing is removable with respect to the bearing component plate through configuration of at least one and preferably, but not necessarily, both ends of the bearing component plate.

BRIEF DESCRIPTION OF THE DRAWINGS

The above mentioned and other features, advantages and objects of this invention, and the manner of attaining them, will become apparent and the invention itself will be better understood by reference to the following description of the invention taken in conjunction with the accompanying drawings, wherein.

Figure 1:
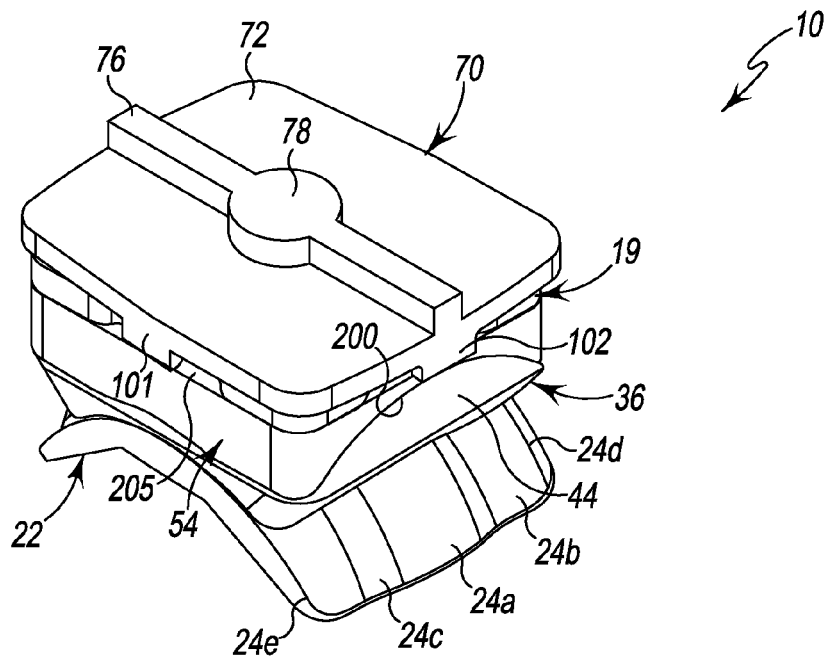
FIG. 1 is an isometric upper view of a left ankle joint replacement implant fashioned in accordance with the principles of the present invention.
Figure 2:
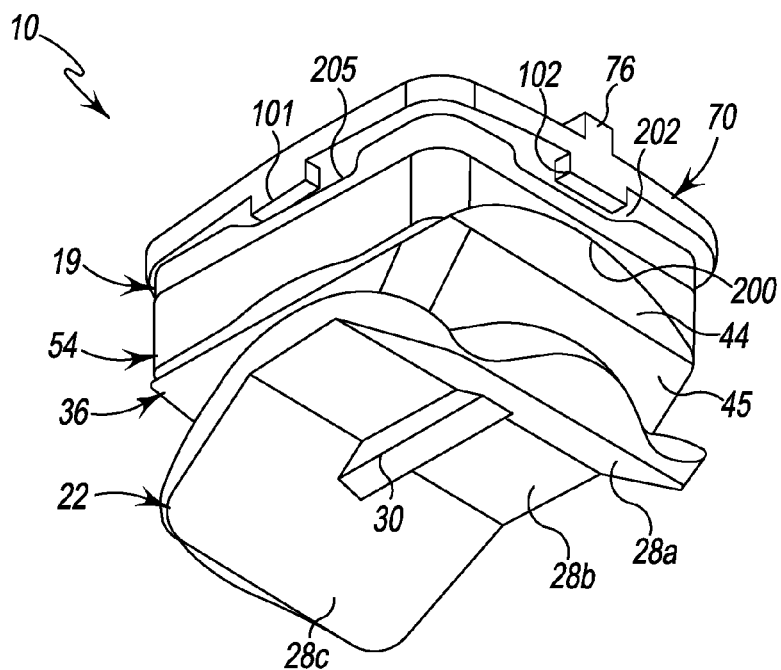
FIG. 2 is an isometric lower view of the left ankle joint replacement implant of FIG. 1.
Figure 3:
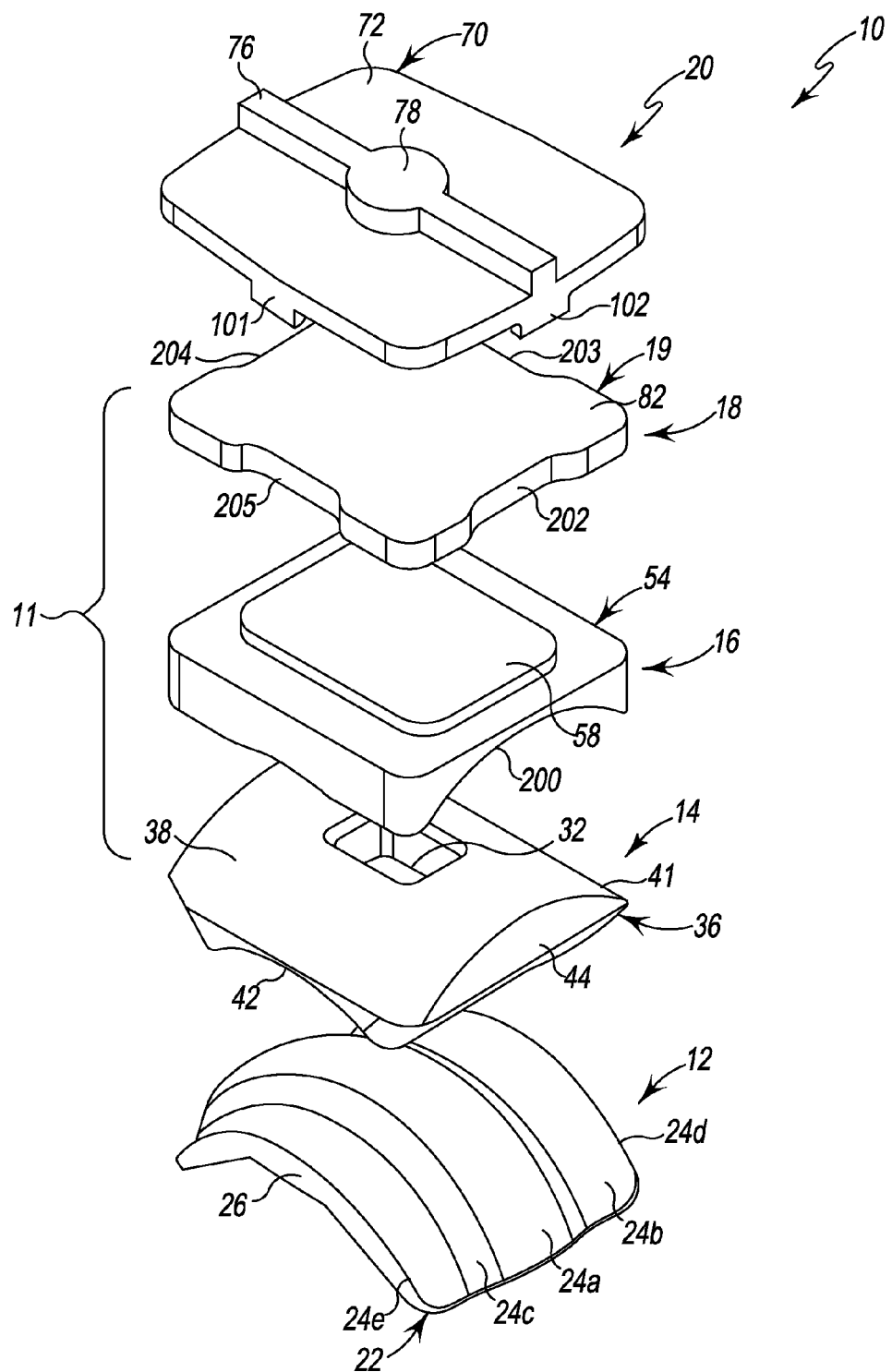
FIG. 3 is an exploded isometric superior view of the left ankle joint replacement implant of FIG. 1.
Figure 4:
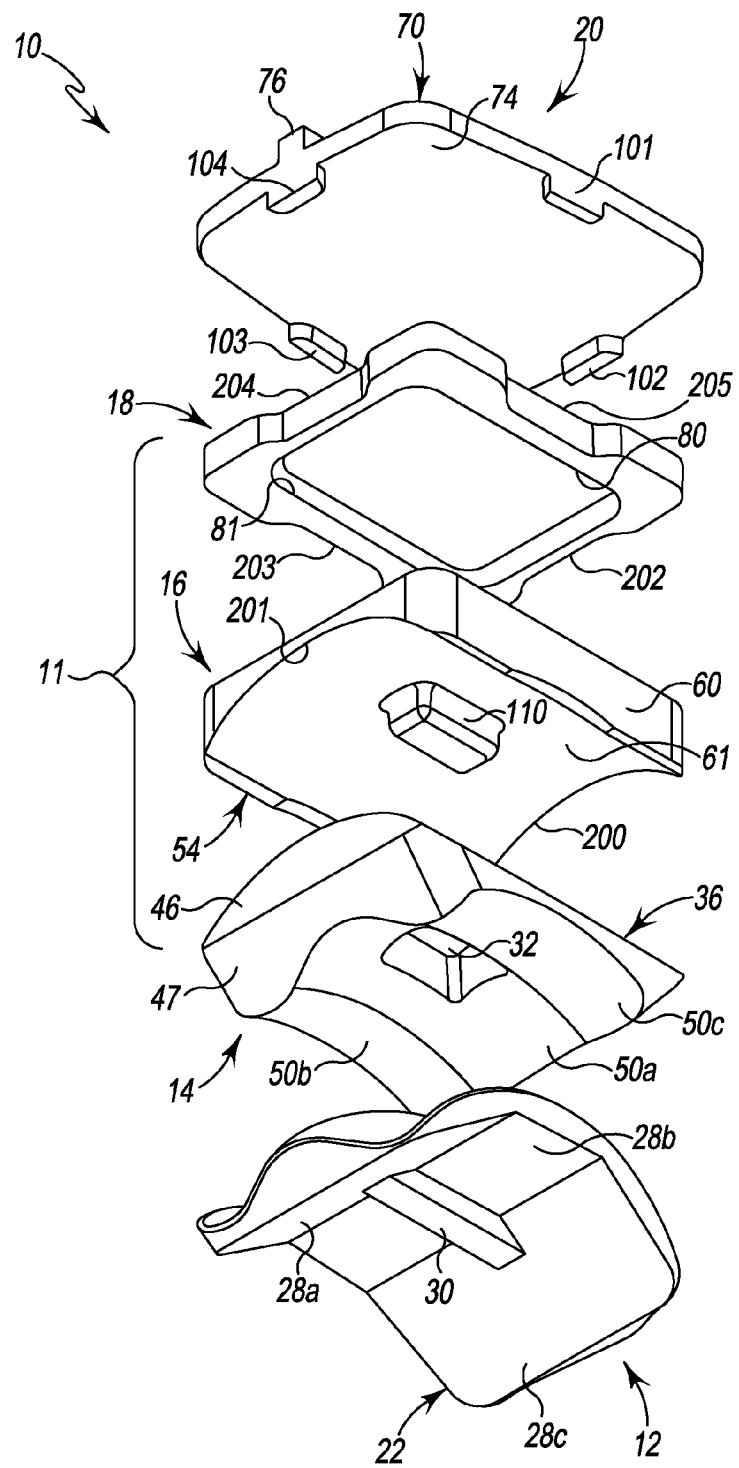
FIG. 4 is an exploded isometric inferior view of the left ankle joint replacement implant of FIG. 1.
Figure 5:
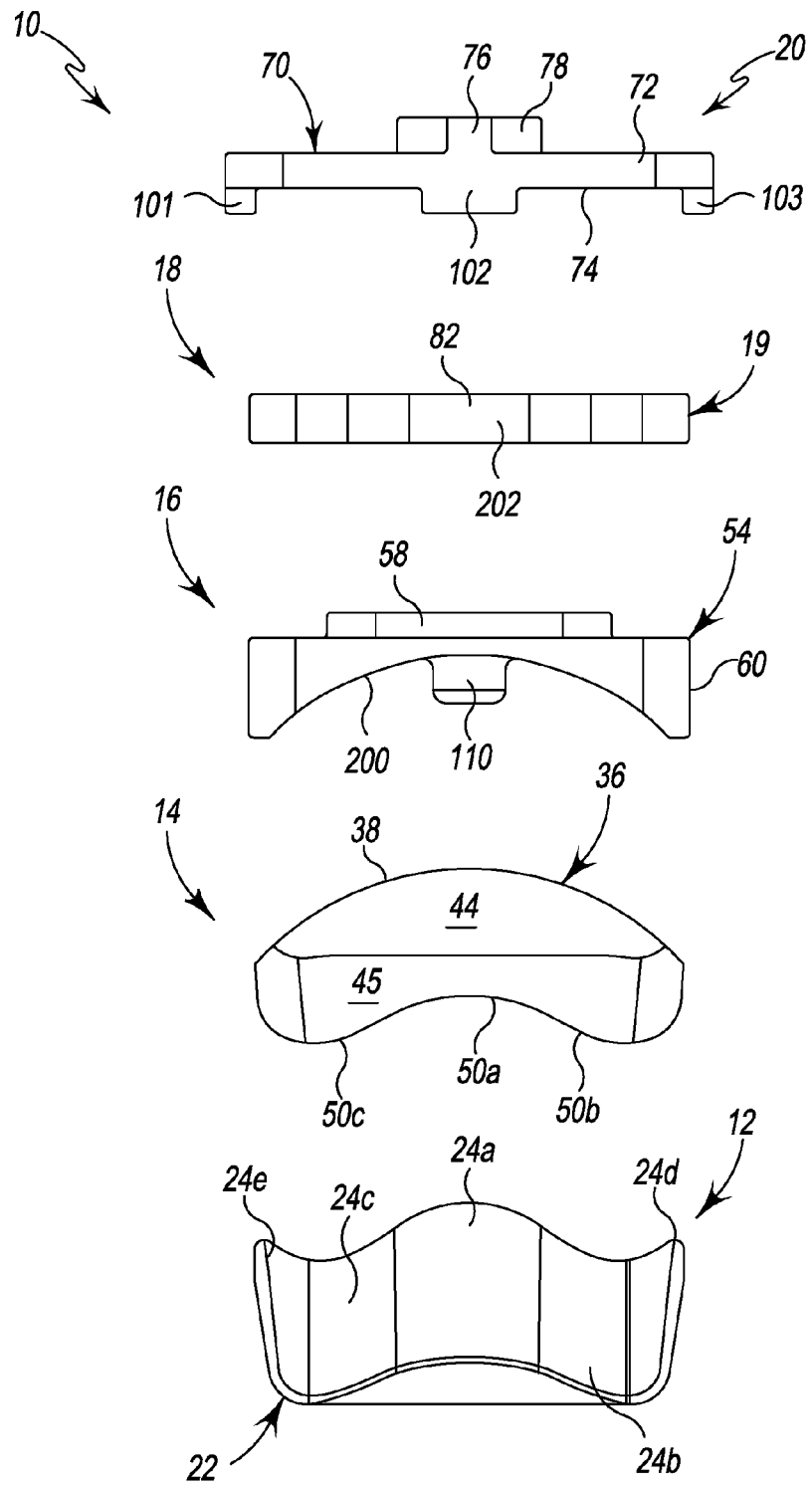
FIG. 5 is an exploded front plan view of the left ankle joint replacement implant of FIG. 1.
Figure 6:
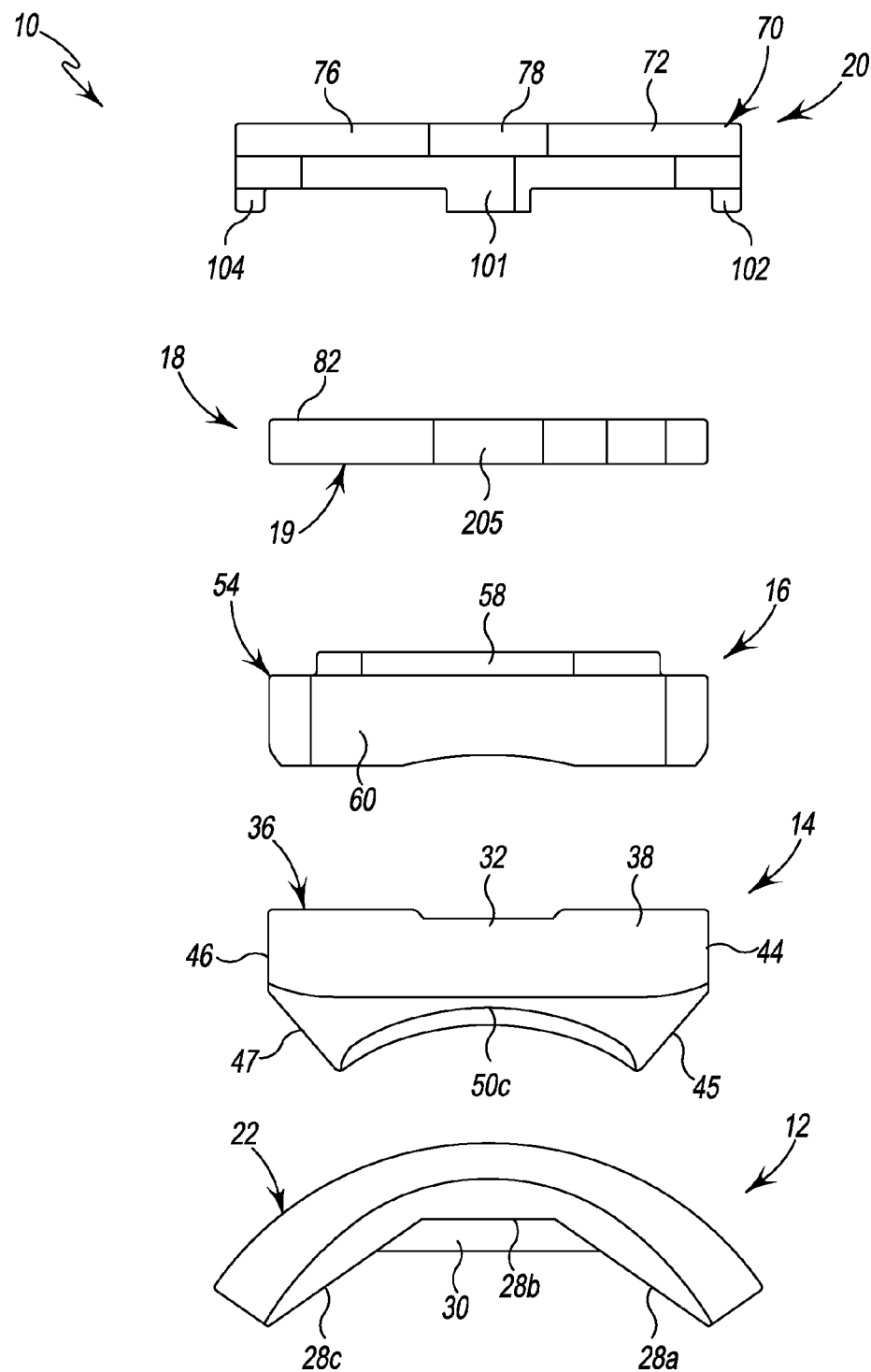
FIG. 6 is an exploded lateral plan view of the left ankle joint replacement implant of FIG. 1.
Figure 7:
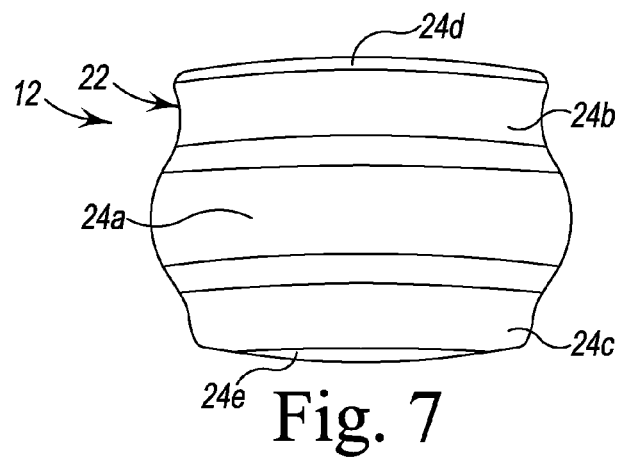
FIG. 7 is a superior plan view of the talus anchoring component of the left ankle joint replacement implant of FIG. 1.
Figure 8:
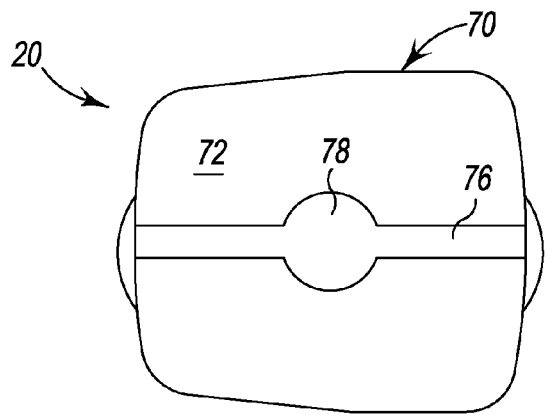
FIG. 8 is a superior plan view of the tibia anchoring component of the left ankle joint replacement implant of FIG. 1.
Figure 9:
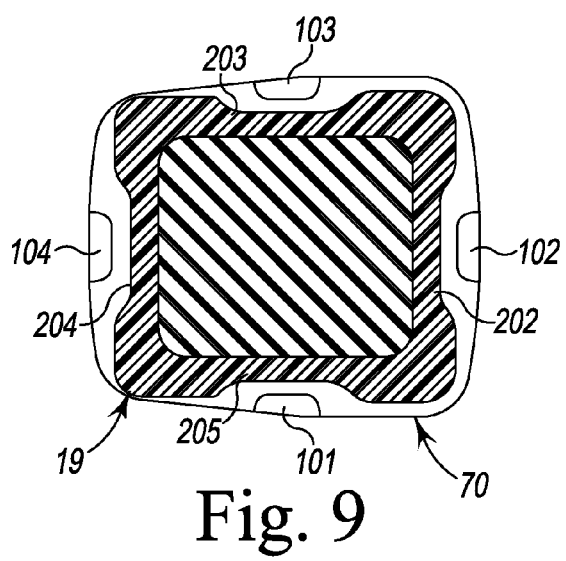
FIG. 9 is a sectional view of the present left ankle joint replacement implant taken along line 9-9 of FIG. 13.
Figure 10:
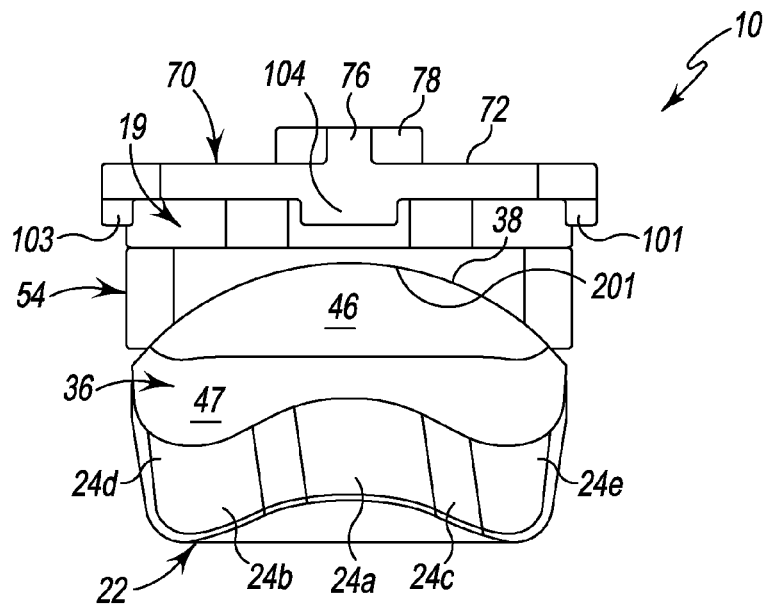
FIG. 10 is a posterior view of the left ankle joint replacement implant of FIG. 1.
Figure 11:
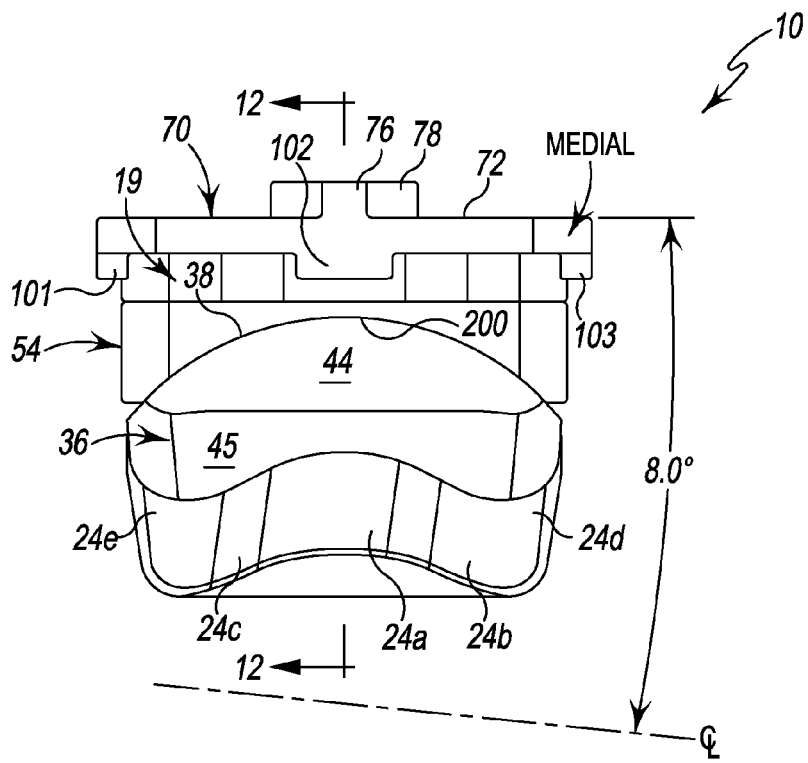
FIG. 11 is an anterior view of the left ankle joint replacement implant of FIG. 1.
Figure 12:
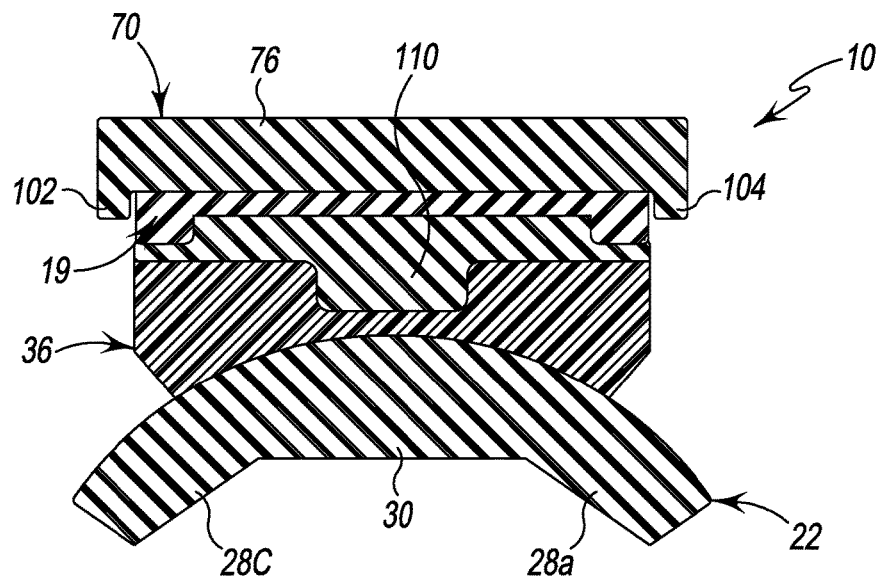
FIG. 12 is sectional view of the present left ankle joint replacement implant taken along line 12-12 of FIG. 11.
Figure 13:
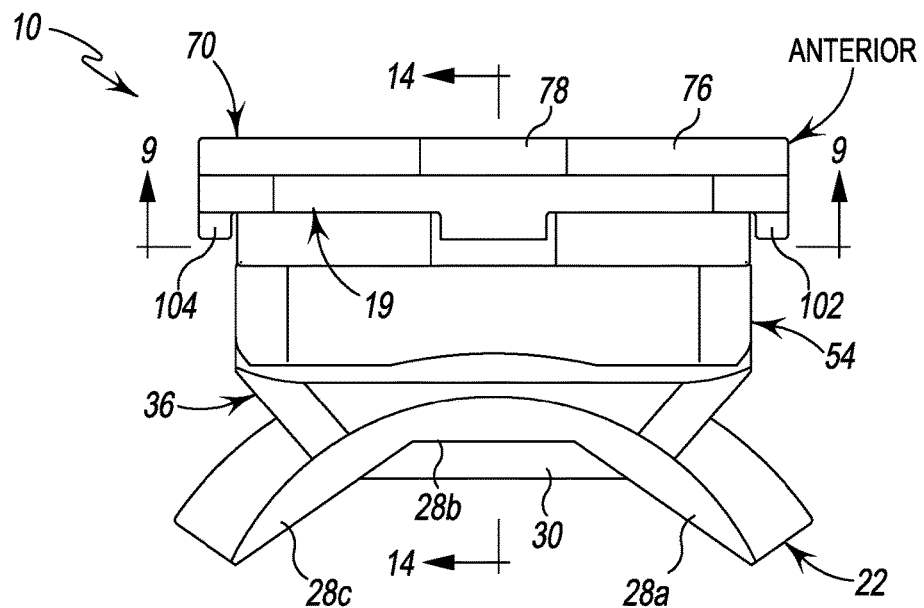
FIG. 13 is a lateral view of the left ankle joint replacement implant of FIG. 1.
Figure 14:
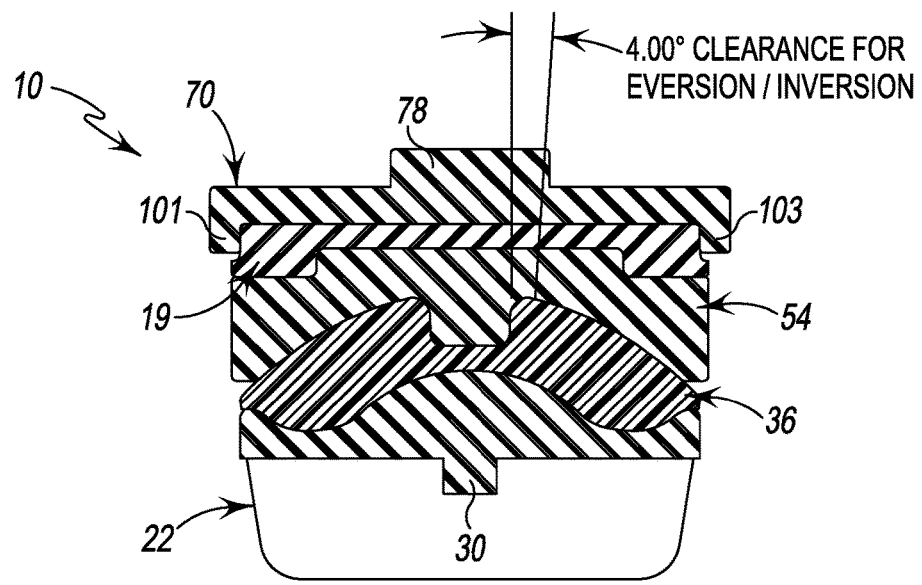
FIG. 14 is a sectional view of the present left ankle joint replacement implant taken along line 14-14 of FIG. 13.
Figure 15:
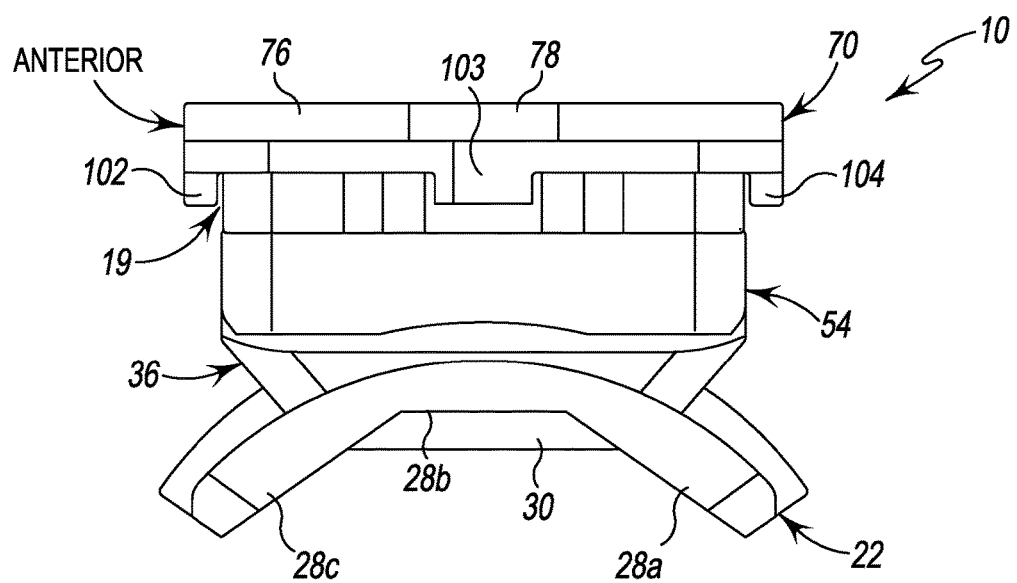
FIG. 15 is another lateral view of the left ankle joint replacement implant of FIG. 1.

Like reference numerals indicate the same or similar parts throughout the several figures. A detailed description of the structures, features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF THE INVENTION

An ankle joint replacement implant or prosthesis 10 provides post-operative interchangeability between a fixed bearing type and a mobile bearing type (and vice versa) without disturbing the metal to bone interfaces/anchoring components for the tibia and the talus, as well as providing post-operative interchangeability between mobile bearings thereby allowing different degrees of freedom (translation).

A left ankle joint replacement implant is shown in the figures. Its principles are of course applicable to a right ankle joint replacement implant, the right ankle joint replacement implant being a mirror image. The present ankle joint replacement implant 10 includes a tibia/tibial anchoring component 20 formed of a biocompatible metal such as stainless steel, titanium, an alloy of same, or other biocompatible material that is attachable to the tibia, and a talus/talar anchoring component 12 formed of a biocompatible metal such as stainless steel, titanium, an alloy of same or other biocompatible material. A dual bearing component 11, composed of three parts; a bearing plate 16, an inferior bearing 14, and a superior bearing 18 is provided between the tibia anchoring component 20 and the talus anchoring component 12. As described herein, one or more of these bearing components, but preferably one bearing component (i.e. the inferior bearing 14), may be swapped out for a fixed bearing from a mobile bearing and vice versa, as well as between mobile bearings of different degrees of freedom/translation.

The inferior and superior bearings 14, 18 may be formed of a biocompatible plastic such as polyethylene, polyetheretherketone (PEEK), polytetrafluoroethylene (PTFE), another biocompatible plastic, or other biocompatible material that provides a gliding bearing surface. The tibia and talus anchoring components 20, 12 as well as the plate 16 of the dual bearing component 11 may be formed of a biocompatible metal such as titanium, stainless steel, an allow thereof, or the like.

Referring to FIGS. 1-19, there is depicted a polyaxial ankle joint replacement implant or prosthesis 10 fashioned in accordance with the present principles. The polyaxial endoprosthetic ankle joint replacement implant 10 (ankle joint replacement implant 10) has several components that interact to provide an ankle replacement implant which mimics a natural ankle joint (i.e. as between the tibia and the talus/calceneus). Particularly, the ankle joint replacement implant 10 includes a talus anchoring component or plate 12 that is configured for attachment to the talus or calceneus bone (not shown), a tibia anchoring component or plate 20 that is configured for attachment to the tibia bone (not shown), and a dual bearing component 11 situated between the talus anchoring component 12 and the tibia anchoring component 20 that is configured to allow articulation or translation with respect to the talus anchoring component 12.

The tibia anchoring component 20 includes a plate 70 and other features described herein, formed of a biocompatible metal such as stainless steel, titanium, an alloy of same, or other biocompatible material. The plate 70 is generally rectangular in shape except that it narrows slightly from the anterior side of the plate 70 to the posterior side of the plate 70. The plate 70 has a generally planar and smooth superior surface 72 and a generally planar and smooth inferior surface 74. Alternatively or additionally, the superior surface 72 may be textured, porous or otherwise if desired to promote bone ingrowth and/or have a slight convex or concave contour. The superior surface 72 has a ridge or projection 76 that extends from and between the anterior side and the posterior side of the plate 70. The ridge 76 is generally rectangular in cross section along its length and serves to prevent or guard against twisting after implantation. The ridge 76 may take shapes other than rectangular. Furthermore, the ridge 76 may not extend entirely from the posterior edge of the plate 70 to the anterior edge of the plate 70. Moreover, the ridge 76 may not be continuous but instead be comprises of two or more segments. Other configurations and arrangements are contemplated. A boss 78 is provided central to the ridge 76 that aids in anchoring the plate 70 into the tibia and preventing rotation.

The tibia plate 70 includes a medial flange 101 that extends downwardly from the medial edge thereof (i.e. is transverse to the plane of the plate 70), a lateral flange 103 that extends downwardly from the lateral edge thereof (i.e. is transverse to the plane of the plate 70), a posterior flange 104 that extends downwardly from the posterior edge thereof (i.e. is transverse to the plane of the plate 70), and an anterior flange 102 that extends downwardly from the anterior edge thereof (i.e. is transverse to the plane of the plate 70). The peripheral tibia flanges 101, 102, 103, 104 semi constrain or limit movement between it and the superior bearing 18.

The talus anchoring component 12 includes a plate 22 formed of a biocompatible metal such as stainless steel, titanium, an alloy of same or other biocompatible material. The talus plate 22 is generally in the shape of an arc that mimics the articulation or translation arc of the natural human ankle joint. The talus plate 22 also narrows slightly from an anterior side of the talus plate 22 to the posterior side of the talus plate 22. The talus plate 22 has a smooth superior surface with several contours 24*a*, 24*b*, 24*c*, extending from and between the anterior and posterior sides of the talus plate 22. The superior surface has an intermediate convex contour 24*a*, a medial concave contour 24*c* and a lateral concave contour 24*b*. The medial side of the talus plate 22 has an arced ledge 24*e* while the lateral side of the talus plate 22 also has an arced ledge 24*d*. The arced ledges support and allows translation of a portion of the tibia thereon. The arched ledges allow a portion of an inferior bearing 14 of the dual bearing component 11 to translate thereon.

The superior surface 24 of the talus plate 22 is angled upwardly from the medial side to the lateral side or conversely angled downwardly from the lateral side to the medial side along the anterior to posterior arcuate length of the talus plate 22. In a preferred form, this angle is around 7.5° however, the angle may be more or less than 7.5°. The angle mimics the natural arch of the ankle.

The inferior surface 28 of the talus plate 22 has three generally planar and smooth arcuate sections or cuts 28*a*, 28*b*, 28*c* that together form the plate arch.

These sections or cuts correspond to the bone cuts in the prepared talus (or calceneal) bone. Alternatively or additionally, the inferior surface may be textured, porous or otherwise if desired to promote bone ingrowth. A ridge or projection 30 extends from section of the inferior surface between the sections. The ridge 30 is generally rectangular in cross section along its length and serves to prevent or guard against twisting after implantation. The ridge 30 may take shapes other than rectangular. Preferably, but not necessarily, the talus anchoring component 12 is machined or made from a single mass of the desired biocompatible material.

The dual bearing component 11 is composed of three parts; a bearing plate 16, an inferior bearing 14, and a superior bearing 18. The bearing plate 16 is defined by a plate 54 formed of a biocompatible metal such as stainless steel, titanium, an alloy of same or other biocompatible material. The plate 54 is generally in the shape of a rectangle and sized to fit under the tibia plate 70. A superior surface of the plate 54 includes a generally rectangular projection 58 that extends in the superior direction. The projection 58 is depicted as rectangular but may take other shapes as desired. Moreover, while a single projection is shown, more projections may be provided.

The bearing plate 54 includes a rim 60 that extends about the periphery of the bearing plate 54 and projects in the inferior direction (i.e. transverse to the plane of the superior surface). An inferior surface 61 of the bearing plate 54 is arced or curved from a medial side thereof to a lateral side thereof within the peripheral rim 60. As such, an arced anterior end 200 is formed at the anterior end of the peripheral rim 60 and an arced posterior end 201 is formed at the posterior end of the peripheral rim 60. The peripheral rim 60 may have a first arced flat at the medial side and a second arced flat at the lateral side if desired. The curved inferior surface 61, the peripheral rim 60 and the anterior and posterior ends 200, 201 provide a pocket that receives the inferior bearing 14 and which allows the inferior bearing 14 to be removed and replaced post-operative during a subsequent operation in order to change out a mobile eversion/inversion inferior bearing to a fixed eversion/inversion inferior bearing, a fixed eversion/inversion inferior bearing to a mobile eversion/inversion inferior bearing, or a mobile eversion/inversion inferior bearing providing a particular degree of inversion/eversion freedom/translation to a mobile eversion/inversion inferior bearing providing a different particular degree of freedom/translation.

The bearing plate 54 further includes a protrusion 110 projecting from the inferior surface 61 that is situated generally in the middle thereof. However, the protrusion 110 may be positioned in other locations if desired. The protrusion 110 is fashioned as a rectangle. However, other shapes may be used.

The superior bearing 18 of the dual bearing component 11 is defined by a plate 19 formed of a biocompatible plastic such as polyethylene, polyetheretherketone (PEEK), polytetrafluoroethylene (PTFE), another biocompatible plastic, or other biocompatible material that provides a gliding bearing surface. The superior bearing plate 19 is generally in the shape of a rectangle and sized to fit onto the superior surface of the bearing plate 54. The superior bearing plate 19 has a generally planar and smooth superior surface 82 and a generally planar and smooth inferior surface 80. The inferior surface 80 is recessed within a wall 81 such that the inferior surface 80 is sized and shaped in like dimension as the protrusion 58 of the plate 54 in order to allow the protrusion 58 to be received in the rectangular recess/inferior surface 80 to provide secure connectivity of the superior bearing component 16 to the plate 54. The superior bearing 18 is preferably, but not necessarily, bonded to the bearing plate 54. The plate 19 further has notches 202, 203, 204, 204 on sides thereof to accommodate the flanges 101, 102, 103, 104 of the tibia anchoring component 20.

The inferior bearing 14 of the dual bearing component 16 is defined by an inferior bearing plate 36 formed of a biocompatible plastic such as polyethylene, polyetheretherketone (PEEK), polytetrafluoroethylene (PTFE), another biocompatible plastic, or other biocompatible material that provides a gliding bearing surface. The inferior bearing plate 36 is generally in the shape of a rectangle but narrows slightly from the anterior side 44 thereof to the posterior side 46 thereof the plate 36. A superior side 38 of the inferior bearing plate 36 is smooth and arced from a lateral side 41 to a medial side 42 thereof. The arc of the superior side 38 corresponds to the arc of the inferior side 61 of the bearing plate 54

The anterior side 44 of the inferior bearing plate 36 is generally arc shaped and corresponds to the arced anterior inside edge of the bearing plate 54. Likewise, the posterior side 46 of the inferior bearing plate 36 is generally arc shaped and corresponds to the arced posterior inside edge of the bearing plate 54. Moreover, the anterior side 44 has a lower angle 45 that angles inwardly towards the inferior surface. Likewise, the posterior side 46 has a lower angle 47 that angles inwardly towards the inferior surface.

The superior side of the talus anchoring component 12 thus includes first and second sagittal longitudinal concave grooves 24b, 24c extending from the anterior side to the posterior side and a first sagittal longitudinal convex ridge 24a situated between the first and second sagittal longitudinal concave grooves 24b, 24c. A radius of the first and second sagittal longitudinal concave grooves and of the first sagittal longitudinal convex ridge vary with a minor arc existing laterally and becoming greater medially for anatomic-like tracking of the talus anchoring component 12 relative to the inferior bearing 14. A medial side 24d is generally convex relative to the concave groove 24b, while a lateral side 24e is generally convex relative to the concave groove 24c.

The upper part 38 of the inferior bearing plate 36 is thus sized to fit into the pocket or area formed by the curved inferior surface 61, the peripheral rim 60 and the anterior and posterior ends 200, 201 of the plate 54. The inferior bearing 36, however, is not bonded to the plate 54 but is relatively free to translate in the medial/lateral directions relative to the plate 54 to provide inversion and eversion.

The ledge 60 may be considered a tracking ledge that extends inferiorly around the periphery of the inferior bearing 14 located in both the anterior and posterior aspects. The tracking ledge 60 of the bearing component plate 54 that catches, guides and prevents the inferior bearing 14 from dislodging from the bearing component plate 54 in the anterior and posterior directions.

The inferior surface of the inferior bearing 14 is generally smooth with several contours 50a, 50b, 50c extending from and between the lower angle 45 of the anterior side 44 and the lower angle 47 of the posterior side 46 of the plate 36. The inferior surface has an intermediate concave contour 50a, a medial convex contour 50c, and a lateral convex contour 50b. The contours correspond oppositely to the contours of the superior surface of the talus anchoring component 22. Particularly, the contours of the inferior bearing 14 fit into the contours of the talus anchoring component 12. This allows translation or articulation between the talus anchoring component 12 and the inferior bearing 14.

The dual bearing component 11 thus provides an inferior bearing surface for the talus anchoring component 12 that allows articulation/translation of the talus anchoring component 12 relative to the dual bearing component 11 in order to provide/allow dorsiflexion and plantar flexion. The talus anchoring component 12 provides up to 25° dorsiflexion relative to the pivot point (vertical centerline of the tibia anchoring component 12) for the talus anchoring component (see e.g., FIGS. 18 and 19). This allows up/down movement of the foot.

Figure 16:
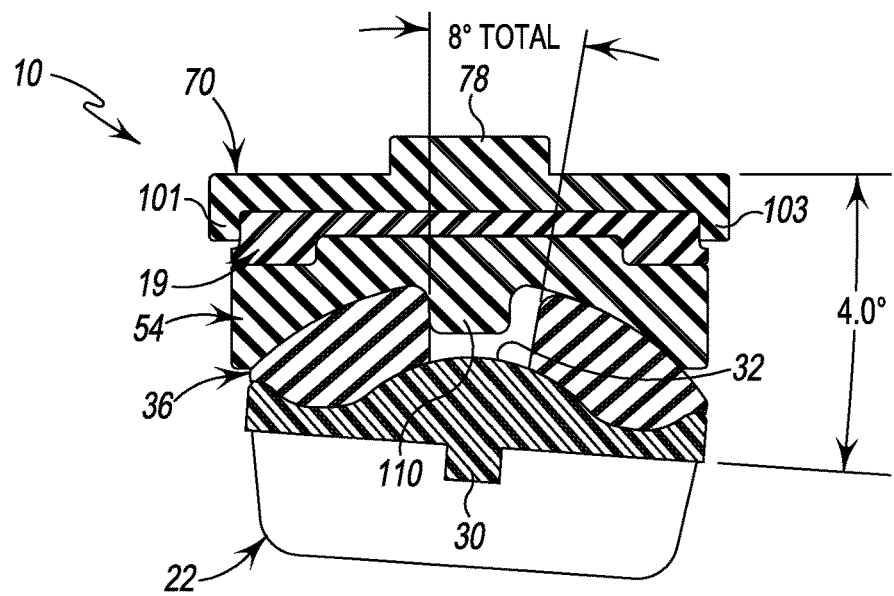
FIG. 16 is a sectional view of the present left ankle joint replacement implant illustrating 4° eversion translation of an inferior bearing's 8° eversion/inversion translation.
Figure 17:
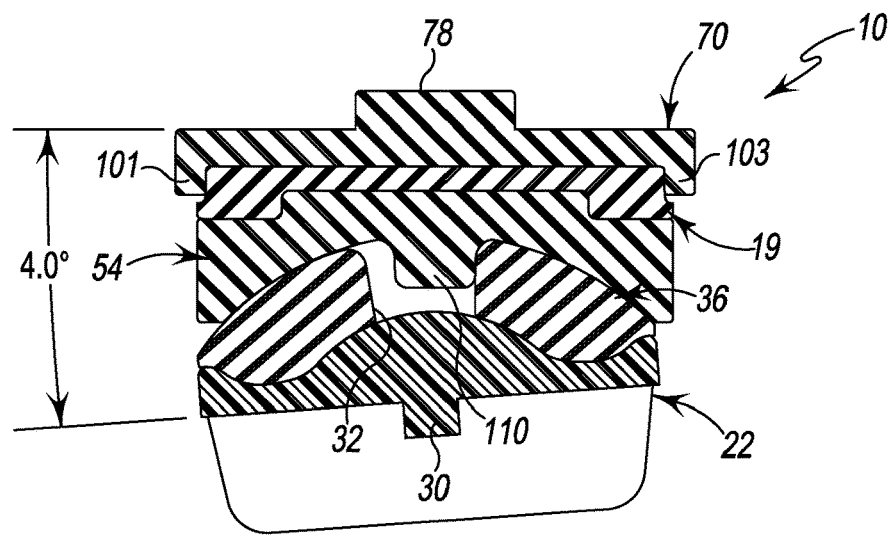
FIG. 17 is a sectional view of the present left ankle joint replacement implant illustrating 4° inversion translation of an inferior bearing's 8° eversion/inversion translation.
Figure 18:
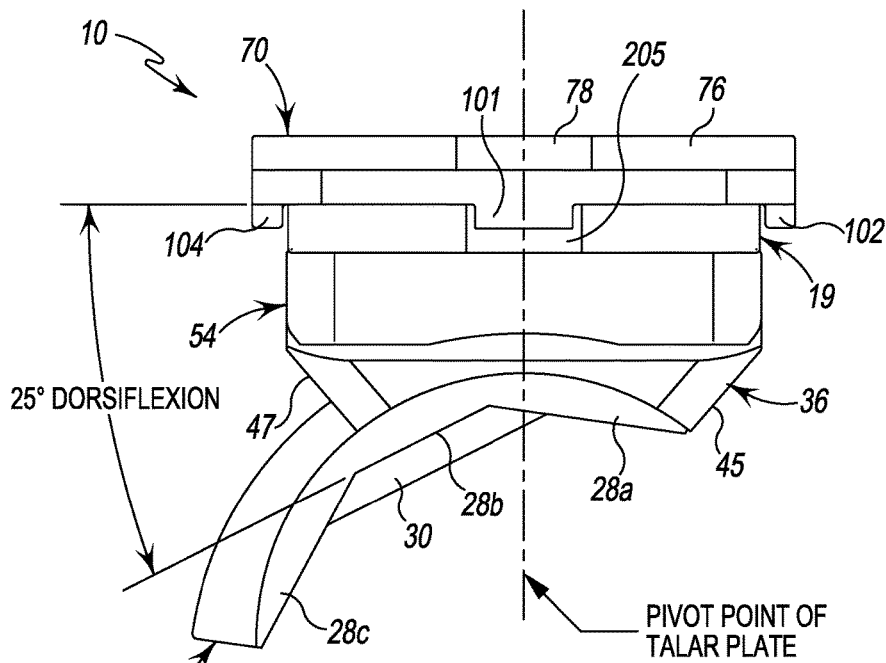
FIG. 18 is a lateral view of the present left ankle joint replacement implant illustrating its 25° dorsiflexion translation with respect to the pivot point of the talar/talus anchoring component.
Figure 19:
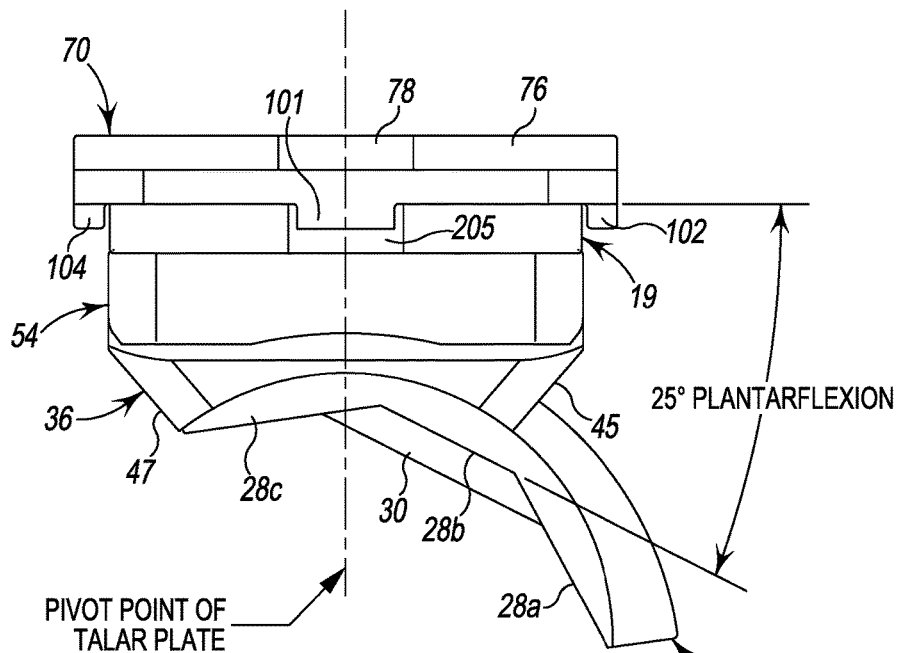
FIG. 19 is a lateral view of the present left ankle joint replacement implant illustrating its 25° plantar flexion translation with respect to the pivot point of the talar/talus anchoring component.

The inferior bearing 14 has a cutout or hole 32 situated generally in the middle of the bearing body 36. The cutout 32 is configured to receive the protrusion 110 of the plate 54 to semi constrain and/or limit eversion/inversion movement between the two components. The size of the cutout 32 determines the amount or degree of eversion/inversion freedom/translation of the implant. As shown in FIGS. 16-17, the inferior bearing 14 of FIGS. 1-19 provides 4° of eversion and 4° of inversion for a total of 8° of freedom. Per the principles of the present invention, the inferior bearing 14 may be swapped out post-operative for another inferior bearing (mobile or fixed) via a subsequent surgery without compromising the tibia anchoring component 20 relative to the tibia, or the talus anchoring component 12 relative to the talus.

Figure 20:
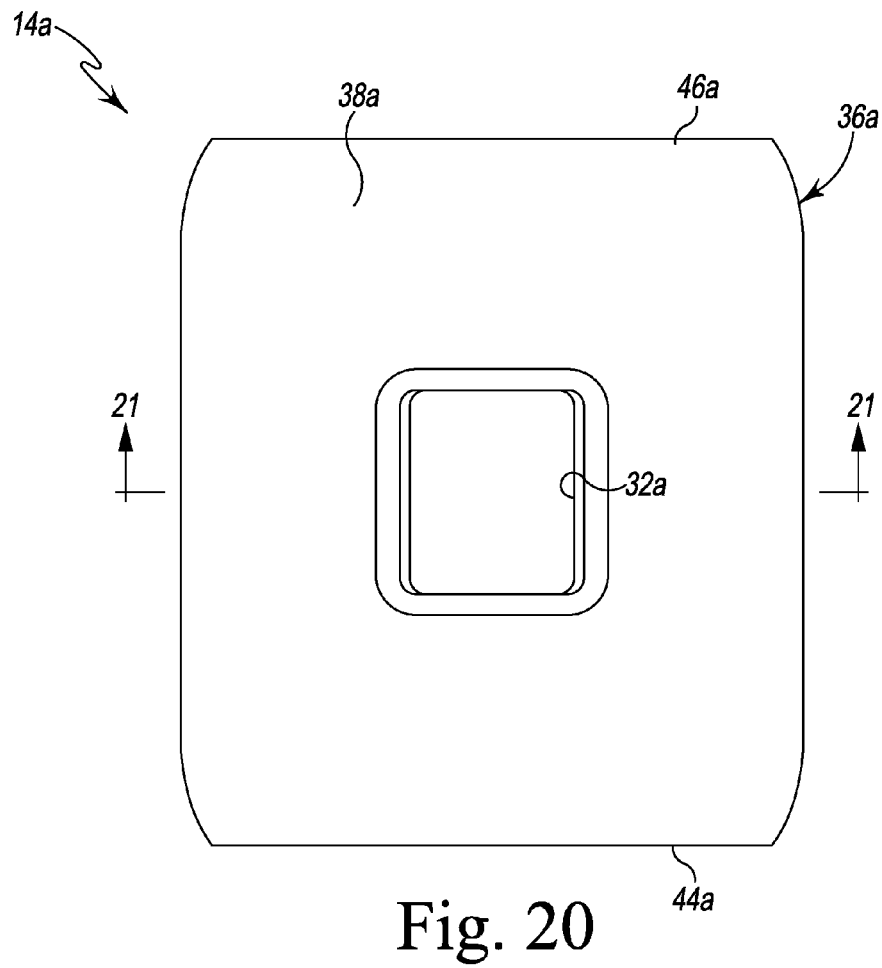
FIG. 20 is a superior plan view of a replacement inferior bearing for the dual bearing component of the present left ankle replacement implant providing a 12° eversion/inversion translation for the ankle joint replacement implant (i.e. a mobile bearing)
Figure 21:
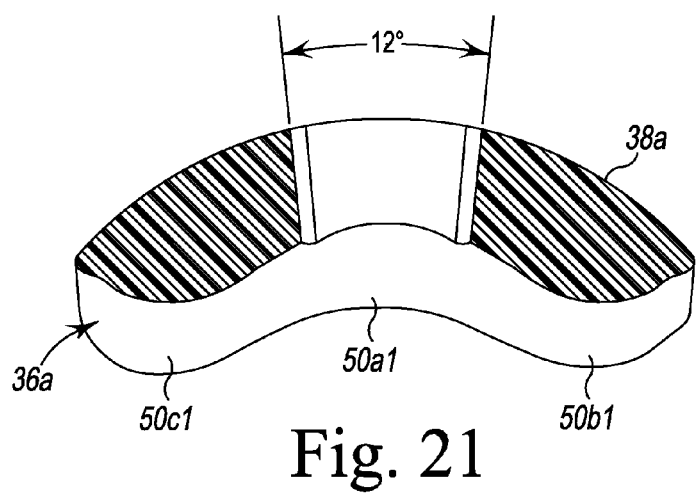
FIG. 21 is a sectional view of the inferior bearing of FIG. 20 taken along line 21-21 thereof.

Referring to FIGS. 20-21, there is shown another inferior bearing 14a having a cutout 32a that provides a total of 12° of eversion/inversion freedom/translation of movement (i.e. 6° of eversion and 6° of inversion). Like features to the inferior bearing 14 are indicated by the designation "a". This is an example of another mobile bearing that may be used and/or swapped out from an existing inferior bearing of an implanted ankle implant 10.

Figure 22:
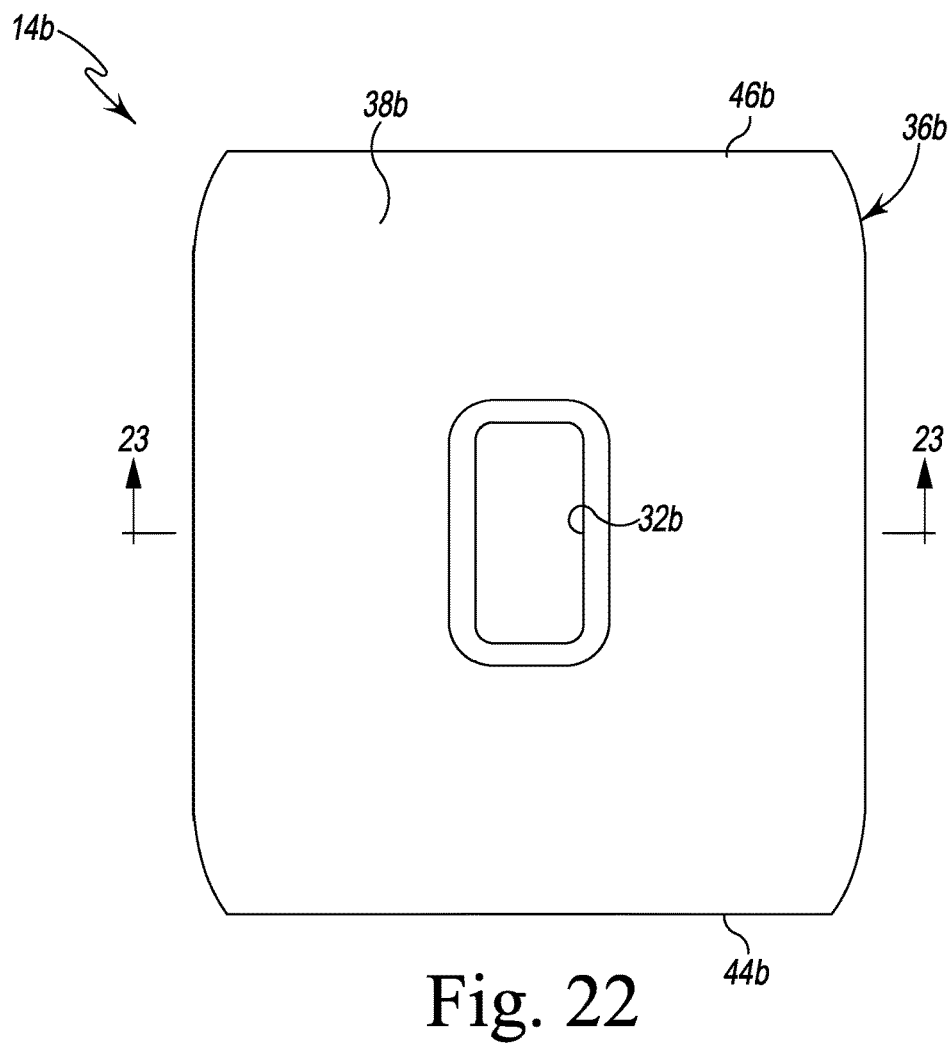
FIG. 22 is a superior plan view of another replacement inferior bearing for the dual bearing component of the present left ankle replacement implant providing a 0° eversion/inversion translation for the ankle joint replacement implant (i.e. a fixed bearing)
Figure 23:
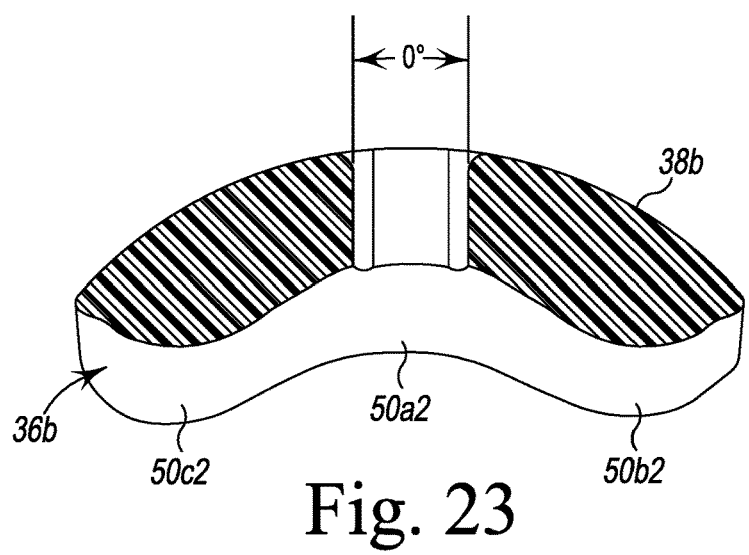
FIG. 23 is a sectional view of the inferior bearing of FIG. 22 taken along line 23-23 thereof.
Figure 24:
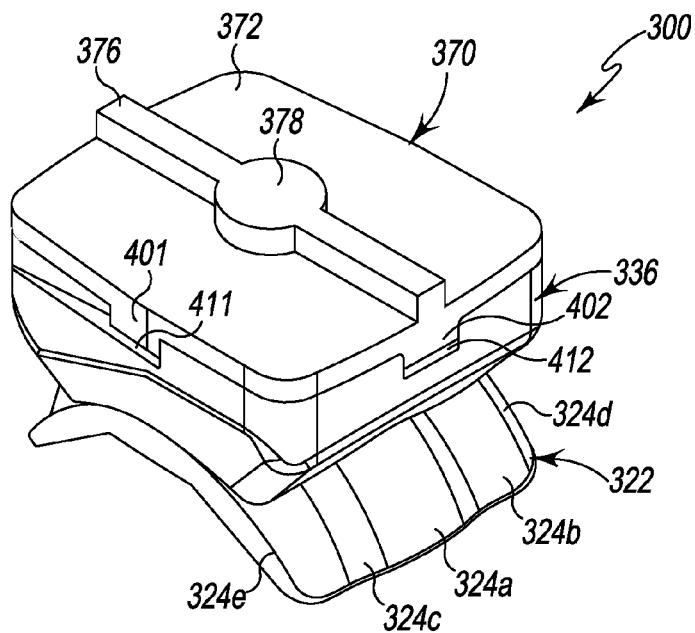
FIG. 24 is an isometric upper view of a 3-piece left ankle joint replacement implant having sagittal plane only motion fashioned in accordance with the principles of the present invention.
Figure 25:
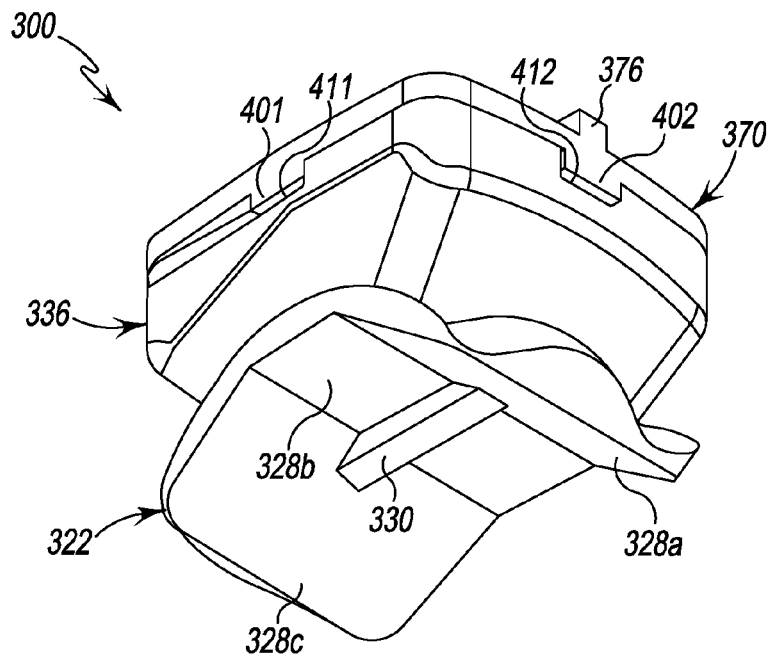
FIG. 25 is an isometric lower view of the 3-piece left ankle joint replacement implant of FIG. 24.
Figure 26:
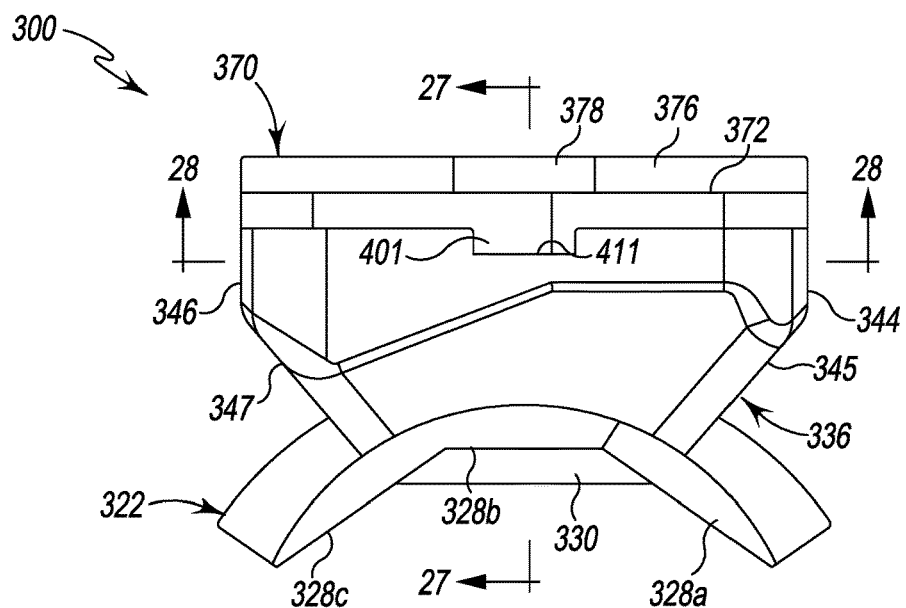
FIG. 26 is a lateral plan view of the 3-piece left ankle joint replacement implant of FIG. 24.
Figure 27:
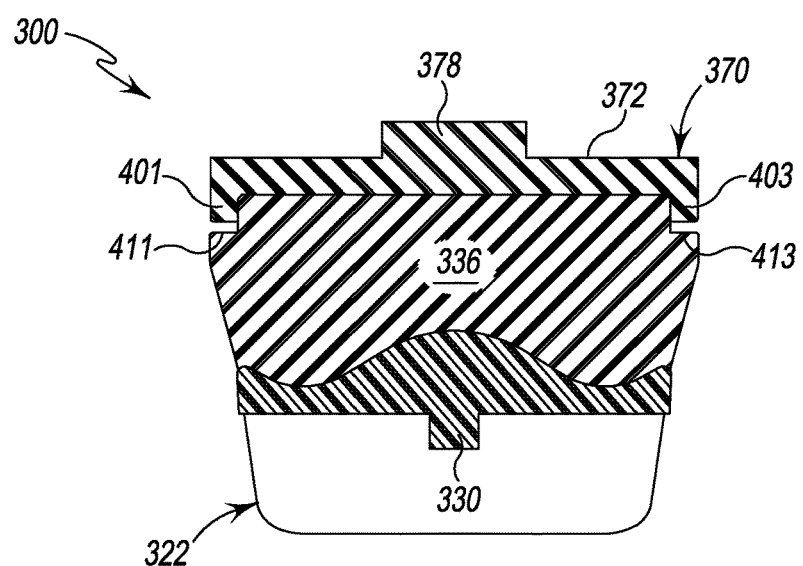
FIG. 27 is a sectional view of the present 3-piece left ankle joint replacement implant taken along line 27-27 of FIG. 26.
Figure 28:
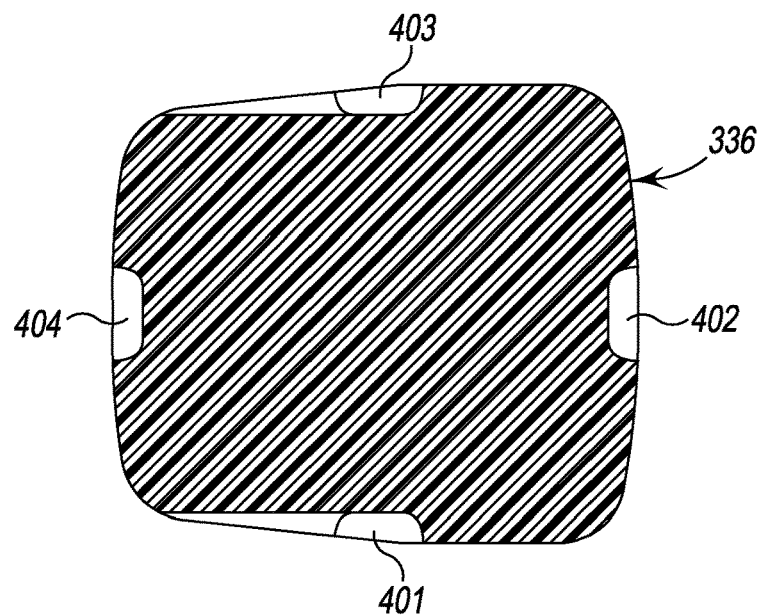
FIG. 28 is a sectional view of the present 3-piece left ankle joint replacement implant taken along line 28-28 of FIG. 26.
Figure 29:
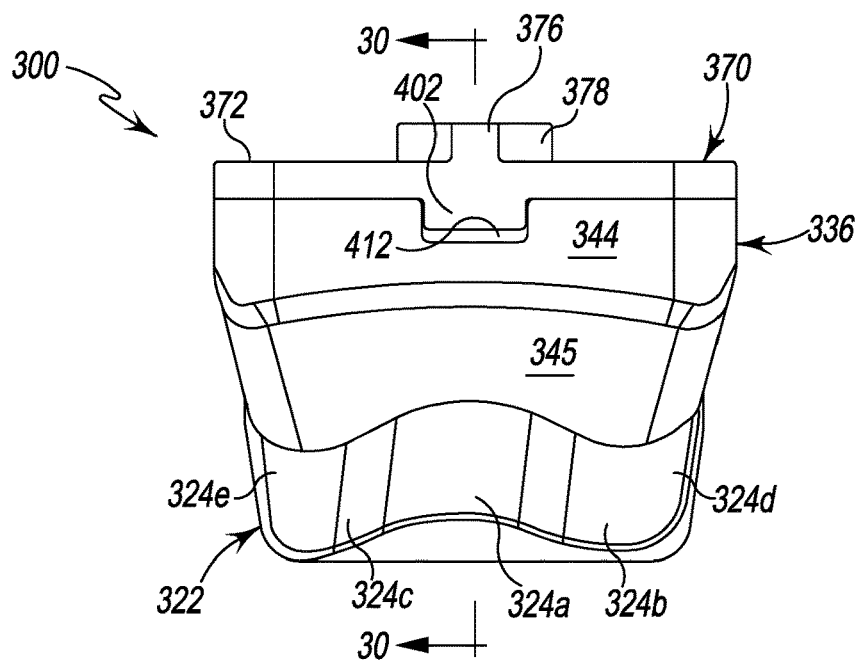
FIG. 29 is a front plant view of the 3-piece left ankle joint replacement implant of FIG. 24.
Figure 30:
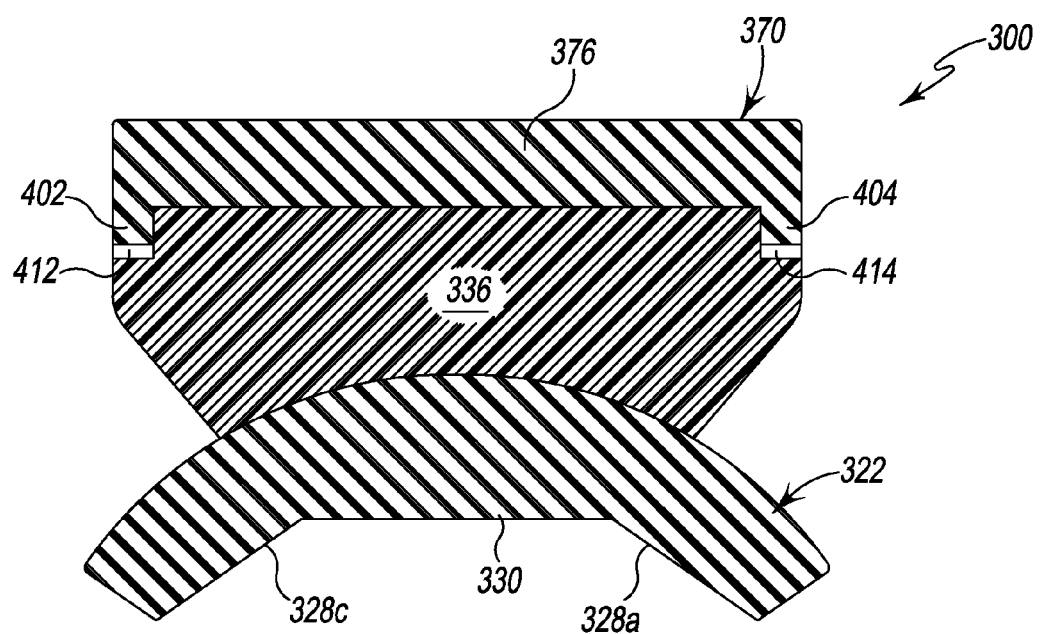
FIG. 30 is a sectional view of the present 3-piece left ankle joint replacement implant taken along line 30-30 of FIG. 29.

Referring to FIGS. 22-23, there is shown another inferior bearing 14b having a cutout 32b that provides a total of 0° of eversion/inversion freedom/translation of movement (i.e. 0° of eversion and 0° of inversion). Like features to the inferior bearing 14 are indicated by the designation "b". This is an example of a fixed bearing that may be used and/or swapped out from an existing inferior bearing of an implanted ankle implant 10.

Referring to FIGS. 24-30, there is shown a 3-piece polyaxial ankle joint replacement implant or prosthesis 300 fashioned in accordance with the present principles. The polyaxial endoprosthetic ankle joint replacement implant 300 (ankle joint replacement implant 300) has several components that interact to provide an ankle replacement implant which mimics a natural ankle joint (i.e. as between the tibia and the talus). Particularly, the ankle joint replacement implant 300 includes a talus anchoring component or plate 370 that is configured for attachment to the talus bone (not shown), a tibia anchoring component or plate 322 that is configured for attachment to the tibia bone (not shown), and a bearing component 336 situated between the talus anchoring component 370 and the tibia anchoring component 322 that is configured to allow articulation or translation with respect to the talus anchoring component 322.

The tibia anchoring component 370 is formed of a biocompatible metal such as stainless steel, titanium, an alloy of same, or other biocompatible material and generally rectangular in shape except that it narrows slightly from the anterior side to the posterior side in like manner to the plate 70 of the ankle implant 10. Other characteristics of the tibia anchoring component 370 are also the same as the plate 70 and thus has a generally planar and smooth superior surface 372 and a generally planar and smooth inferior surface. Alternatively or additionally, the superior surface may be textured, porous or otherwise if desired to promote bone ingrowth and/or have a slight convex or concave contour. The superior surface 372 has a ridge or projection 376 that extends from and between the anterior side and the posterior side thereof. The ridge 376 is generally rectangular in cross section along its length and serves to prevent or guard against twisting after implantation. The ridge 376 may take shapes other than rectangular. Furthermore, the ridge 376 may not extend entirely from the posterior edge thereof to the anterior edge thereof. Moreover, the ridge 376 may not be continuous but instead be comprises of two or more segments. Other configurations and arrangements are contemplated. A boss 378 is provided central to the ridge 376 that aids in anchoring component 370 into the tibia and preventing rotation.

The tibia anchoring component 370 includes a medial flange 401 that extends downwardly from the medial edge thereof (i.e. is transverse to the plane of the plate), a lateral flange 403 that extends downwardly from the lateral edge thereof (i.e. is transverse to the plane of the plate), a posterior flange 404 that extends downwardly from the posterior edge thereof (i.e. is transverse to the plane of the plate), and an anterior flange 402 that extends downwardly from the anterior edge thereof (i.e. is transverse to the plane of the plate). The peripheral tibia anchoring component flanges 401, 402, 403, 404 semi constrain or limit movement between it and the bearing 336. The bearing 336 thus has complementary side cutouts 411, 412, 413, 414.

While not particularly shown, the inferior surface of the bearing 336 is generally smooth with several contours extending from and between the lower angle 345 of the anterior side 344 and the lower angle 347 of the posterior side 346 thereof. The inferior surface has an intermediate concave contour, a medial convex contour, and a lateral convex contour. The contours correspond oppositely to the contours of the superior surface of the talus anchoring component 322. Particularly, the contours of the inferior side of the bearing 336 fit into the contours of the talus anchoring component 322. This allows translation or articulation between the talus anchoring component 322 and the inferior side/surface of the bearing 336.

The talus anchoring component 322 includes a plate formed of a biocompatible metal such as stainless steel, titanium, an alloy of same or other biocompatible material. The talus anchoring component 322 is generally in the shape of an arc that mimics the articulation or translation arc of the natural human ankle joint. The talus plate also narrows slightly from an anterior side thereof to the posterior side thereof. The talus plate has a smooth superior surface with several contours 324a, 324b, 324c, extending from and between the anterior and posterior sides of the talus plate 322. The superior surface has an intermediate convex contour 324a, a medial concave contour 324c and a lateral concave contour 324b. The medial side of the talus plate 322 has an arced ledge 324e while the lateral side of the talus plate 322 also has an arced ledge 324d. The arced ledges support and allows translation of a portion of the tibia thereon. The arched ledges allow a portion of the inferior side of the bearing 336 to translate thereon.

The superior surface of the talus plate 322 is angled upwardly from the medial side to the lateral side or conversely angled downwardly from the lateral side to the medial side along the anterior to posterior arcuate length of the talus plate 322. In a preferred form, this angle is around 7.5° however, the angle may be more or less than 7.5°. The angle mimics the natural arch of the ankle.

The inferior surface of the talus plate 322 has three generally planar and smooth arcuate sections or cuts 328a, 328b, 328c that together form the plate arch. These sections or cuts correspond to the bone cuts in the prepared talus (or calceneal) bone. Alternatively or additionally, the inferior surface may be textured, porous or otherwise if desired to promote bone ingrowth. A ridge or projection 330 extends from section of the inferior surface between the sections. The ridge 330 is generally rectangular in cross section along its length and serves to prevent or guard against twisting after implantation. The ridge 330 may take shapes other than rectangular. Preferably, but not necessarily, the talus anchoring component 322 is machined or made from a single mass of the desired biocompatible material.

It should be appreciated that although the present ankle joint replacement implants set forth herein are described in detail in connection with the ankle joint, the implant and/or principles of the present invention also has application for use with other joints throughout the body, such as for example, both the spine and wrist, with an upper or proximal fixation portion, a dual bearing design, and a lower or distal fixation component.

Moreover, while the invention has been illustrated and described in detail in the drawings and foregoing description, the same is to be considered as illustrative and not restrictive in character, and that all changes and modifications that come within the spirit of the invention are desired to be protected.

What is claimed is:

1. An ankle joint replacement implant comprising:
   a tibial attachment plate configured for attachment to a tibial bone;
   a talar attachment plate configured for attachment to a talar bone; and
   a multi-level modular component interpositional polyaxial bearing positioned between the tibial attachment plate and the talar attachment plate, the multi-level modular component interpositional polyaxial bearing comprising a bearing support plate defining a superior side with a superior surface and an inferior side with an inferior surface, a mostly planar superior bearing having an interior surface reversibly bonded and in contact with the superior side of the bearing support plate, and a curved inferior bearing in contact and either fully non-articulating or articulating with the inferior side of the bearing support plate, the bearing support plate having a flange on the inferior surface, the inferior bearing having an opening sized to receive the flange, the size of the opening of the inferior bearing determining an amount of degree of frontal plane articulation between the bearing support plate and the inferior bearing thereby permitting use of non-articulating and articulating inferior bearings, the bearing support plate of the multi-level modular component bearing having an unobstructed end allowing removal of an implanted articulating or non-articulating inferior bearing and replacement thereof with a non-articulating or articulating inferior bearing opposite to the inferior bearing that is being removed without disturbing attachment of the tibial attachment plate to the tibial bone or the connection of the talar attachment plate to the talar bone.

2. The ankle joint replacement implant of claim 1, wherein the bearing support plate of the multi-level modular component interpositional polyaxial bearing has an unobstructed posterior end allowing removal and replacement of the inferior bearing of the multi-level modular component interpositional polyaxial bearing after installation of the implant without disturbing connection of the tibial attachment plate to the tibial bone or the connection of the talar attachment plate to the talar bone.

3. The ankle joint replacement implant of claim 2, wherein the bearing support plate of the multi-level modular component interpositional polyaxial bearing has an unobstructed anterior end allowing removal and replacement of the inferior bearing of the multi-level modular component interpositional polyaxial bearing after installation of the implant without disturbing connection of the tibial attachment plate to the tibial bone or the connection of the talar attachment plate to the talar bone.

4. The ankle joint replacement implant of claim 3, wherein the inferior bearing of the multi-level modular component interpositional polyaxial is replaceable with an inferior bearing allowing non-articulation with an inferior side of the bearing support plate.

5. The ankle joint replacement implant of claim 3, wherein the inferior bearing of the multi-level modular component interpositional polyaxial bearing is replaceable with an inferior bearing allowing frontal plane only articulation with an inferior side of the bearing support plate.

6. The ankle joint replacement implant of claim 5, wherein the inferior bearing of the multi-level modular component interpositional polyaxial bearing is replaceable with an inferior bearing allowing a limited degree of frontal plane only articulation with the inferior side of the bearing support plate.

7. The ankle joint replacement implant of claim 2, wherein the inferior surface of the superior bearing is reversibly bonded to the superior surface of the bearing support plate and is completely constrained, congruent and non-articulating.

8. The ankle joint replacement implant of claim 1, wherein the tibial attachment plate has a tibial bone integration surface on its superior side and peripheral, transversely extending flanges on each side which extend transversely to a smooth and planar underside of a tibial anchoring surface of the tibial attachment plate that limits transverse plane movement between the inferior surface of the tibial attachment plate and the superior articulating surface of the multi-level modular component interpositional polyaxial bearing.

9. The ankle joint replacement implant of claim 1, wherein the flange on the inferior surface of the bearing support plate is situated in a center of the inferior surface, and the opening of the inferior bearing is situated in a center of the inferior bearing.

10. An ankle joint replacement implant comprising:
a first plate configured for attachment to a tibial bone;
a second plate configured for attachment to a talar bone; and
a multi-level modular component interpositional polyaxial bearing between the first plate and the second plate, the multi-level modular component interpositional polyaxial bearing comprising a bearing support plate having a superior side and an inferior side with a projection situated on the inferior surface, a first bearing on the superior side of the bearing support plate and configured for gliding translation on its superior surface with an inferior surface of the first plate, and a second bearing on the inferior side of the bearing support plate and configured on its inferior surface for gliding articulation with the second plate, the second bearing having an opening sized to receive the inferior projection on the inferior side of the bearing support plate, the size of the opening determining an amount of degree of frontal plane only motion between the bearing support plate and the second bearing, thereby permitting use of a choice of second bearings allowing from no degree of inversion and/or eversion translation between the bearing support plate and the second bearing to a maximum degree of inversion and/or eversion translation between the bearing support plate and the second bearing, the bearing support plate of the multi-level modular component interpositional polyaxial bearing having an unobstructed end allowing removal of an implanted second bearing that allows a first degree of inversion and eversion translation between the bearing support plate and the second bearing of the dual bearing component, and replacement thereof with a second bearing that allows a second degree of inversion and eversion translation between the bearing support plate and the second bearing of the multi-level modular component polyaxial bearing after installation of the implant without disturbing connection of the first plate to the tibial bone or the connection of the second plate to the talar bone.

11. The ankle joint replacement implant of claim 10, wherein the bearing support plate of the multi-level modular component polyaxial bearing has an unobstructed posterior end allowing removal and replacement of the second bearing and/or the first bearing of the multi-level modular component polyaxial bearing after installation of the implant without disturbing connection of the first plate to the tibial bone or the connection of the second plate to the talar bone.

12. The ankle joint replacement implant of claim 11, wherein the bearing support plate of the multi-level modular component polyaxial bearing component has an unobstructed anterior end allowing removal and replacement of the second bearing of the dual bearing component after installation of the implant without disturbing connection of the first plate to the tibial bone or the connection of the second plate to the talar bone.

13. The ankle joint replacement implant of claim 12, wherein the second bearing of the multi-level modular component polyaxial bearing is replaceable with another second bearing allowing 0° of frontal plane motion.

14. The ankle joint replacement implant of claim 12, wherein the second bearing of the multi-level modular component polyaxial bearing is replaceable with another second bearing allowing greater than 0° of frontal plane motion.

15. The ankle joint replacement implant of claim 14, wherein the second bearing of the multi-level modular component polyaxial bearing is replaceable with another second bearing allowing greater than 0° of frontal plane motion but less than 11° of frontal plane motion.

16. The ankle joint replacement implant of claim 11, wherein the first bearing of the multi-level modular component polyaxial bearing is reversibly bonded to the plate.

17. An ankle joint replacement implant comprising:
a first component configured for attachment to a tibial bone,
a second component configured for attachment to a talar bone; and
a dual bearing component between the first component and the second component, the dual bearing component comprising a plate having a superior side and an inferior side with a projection situated on the inferior surface, a first bearing on the superior side of the plate and configured for gliding translation with the first component, and a second bearing on the inferior side of the plate and configured for gliding translation with the second component, the second bearing having an opening sized to receive the projection, the size of the opening determining an amount of degree of inversion and eversion translation between the plate and the second bearing;
wherein the first component has a peripheral, transversely extending flange on each side that limits movement between the first component and the first bearing.

* * * * *